United States Patent [19]

Towns et al.

[11] Patent Number: 5,925,006
[45] Date of Patent: Jul. 20, 1999

[54] SILANE RESINOUS ORTHOPAEDIC CASTING AND SPLINTING MATERIALS

[75] Inventors: Carl Robert Towns, Buntingford; Kevin Andrew Yeomans, Boston Spa, both of United Kingdom

[73] Assignee: Smith & Nephew plc, London, United Kingdom

[21] Appl. No.: 08/875,785

[22] PCT Filed: Feb. 2, 1996

[86] PCT No.: PCT/GB96/00231

§ 371 Date: Sep. 11, 1997

§ 102(e) Date: Sep. 11, 1997

[87] PCT Pub. No.: WO96/23531

PCT Pub. Date: Aug. 8, 1996

Related U.S. Application Data

[30] Foreign Application Priority Data

Feb. 2, 1996 [GB] United Kingdom ................... 9502202

[51] Int. Cl.$^6$ ........................................................ A61F 5/00
[52] U.S. Cl. ........................................................ 602/7; 602/7
[58] Field of Search .................................................. 602/7

[56] References Cited

U.S. PATENT DOCUMENTS 5,540,652   7/1996   Callinan, et al. ............................ 602/1

*Primary Examiner*—Richard J. Apley
*Assistant Examiner*—Kelvin Hart
*Attorney, Agent, or Firm*—Larson & Taylor

[57] ABSTRACT

A curable silane functionalized resin for casting and splinting materials comprising a flexible substrate carrying the resin. The resin is based upon a prepolymer made by nucleophilic addition reactions where at least one reagent is terminated with an alkylenesilane.

18 Claims, No Drawings

SILANE RESINOUS ORTHOPAEDIC CASTING AND SPLINTING MATERIALS

In particular this invention relates to casting and splinting materials based on synthetic resins which, upon contact with water will cross-link and harden to form a weight bearing support for a limb or body portion and to such resins which on contact with water will cross-link and harden.

Resin based splinting and casting materials find wide use in the immobilisation of limbs, for example the fixation of fractured bones, immobilisation of injured joints and for the support of ligaments and muscles where it is necessary to encase the limb in a partially or completely surrounding rigid form or cast.

There are several major considerations for a casting or splinting material. A suitable material should be easily handleable, with a reasonable setting time to allow sufficient time in the case of casting bandages to mould the bandage about the limb and it should be flexible and free of offensive chemicals which may affect the patient or practioner applying the material. In addition it is desirable that during the forming of the cast the material does not generate an uncomfortable exothermic reaction and that it sets within a relatively short time under mild conditions.

Splinting and casting materials comprising water activated synthetic polymers in which a cross-linkable prepolymer resin system is coated onto a suitable substrate are well known. The most favoured and commercially developed systems are those based on prepolymers which contain isocyanate functional groups and which in the presence of cold water will cross-link to form urea bridges. The resin systems usually also contain a catalyst to speed up the cross-linking reaction and so that a weight bearing cast may be formed in as shorter time as possible consistent with requirements for moulding and shaping the splint.

The isocyanate cross linking reaction is usually an exothermic reaction. In meeting the working requirements for such resin systems the resin chemistry has to be carefully controlled so as to allow the resins to cure in a period of time which is acceptably short and yet not cure under conditions in which so much heat is evolved that the applied cast is uncomfortable to the wearer.

A disadvantage of such systems is the relatively high exotherm generated on curing and that there is a perceived health hazard with the use of orthopaedic bandages comprising isocyanate functionalised prepolymers. It is thus desirable to make a suitable splinting materials without utilising isocyanate functionalised prepolymers and thus considerable care has to be taken in both the preparation of the splinting or casting material and in its use to ensure that all the isocyanate functionalities are fully reacted.

In U.S. Pat. No. 4,411,262 (von Bonin et al) there are disclosed splinting and casting materials comprising substrates impregnated or coated with a reactive one component system, wherein inter alia the system includes organic compounds with molecular weights greater than 10,000, comprising reactive groups which may be alkoxysilane groups. It is taught that the organic compounds themselves were produced by an isocyanate functionalised reaction and thus any perceived health risk associated with isocyanate functionalised resins is not entirely removed without ensuring that the resins are fully reacted.

U.S. Pat. No. 5,423,735 also describes materials of this type, where the water reactive resin is an alkoxysilane functionalised polyurethane/polyurea resin, produced by reacting isocyanate functionalised precursors. Such resins potentially have the same problems which may be associated with other prior resins produced from isocyanate functionalised precursors.

The present invention seeks to provide an improved orthopaedic casting bandage with a one component resin system which completly avoids the use of free isocyanate groups as the water activated reactive groups, thus eliminating any health hazard which may be associated with the use of materials containing free isocyanate groups.

Although the splinting and casting material of the present invention is described in terms of "an orthopaedic casting bandage", the term is also intended to embrace splints and braces, where such splints and braces do not necessarily surround the whole limb or other body portion.

In accordance with the present invention there is provided an orthopaedic casting bandage comprising a flexible substrate carrying a water curable silane functionalised resin system, characterised in that the resin system comprises a prepolymer having a general formula (I):

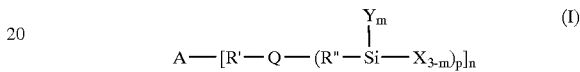

(a) wherein A is a polymeric residue, optionally interrupted by

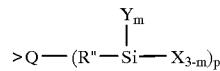

(b) X comprises a water hydrolysable alkoxy or acyloxy group based on $C_1$ to $C_6$ hydrocarbon group
(c) Y is H, alkyl, aryl, halide, X based on $C_1$ to $C_6$ hydrocarbon group
(d) n=1 to 20, m=0 to 2, p=1 to 2
(e) Q comprises residues based on the following formulae (II)

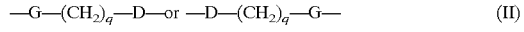

where G=—CH(OH)—, —C(O)—, —CH(NH$_2$)—, —CH(SH)— and D is —NH—, —N<, —O—, —S— and q=1 or 2
(f) R' and R" may be the same or different, substituted or unsubstituted and are are groups based on the following $C_1$–$C_{12}$ alkylene, arylene, cycloalkylene, heteroalkylene, heteroarylene, heterocycloalkylene all of which may be optionally interrupted by —O—, —S—, —Ne—, —C(O)—, further units of Q, with the proviso that urea —NHC(O)NH—, urethane —NHC(O)—, carbamylthio —SC(O)NH— are not represented.

The prepolymers employed in the present invention are end capped with a silane residue containing a hydrolysable group (X). Aptly the hydrolysable group is an alkoxy or acyloxy group.

Favoured end capping groups have the general formula —Si(OR)$_n$, —Si(OCOR)$_n$, —Si—O—Si(OR)$_n$, —Si—O—Si(R$_1$)$_{3-n}$(OR)$_n$, —Si(OC(R$_3$)=C(R$_1$)(R$_2$)$_n$, where n has a maximum value of 3 and each of R, R$_1$, R$_2$ and R$_3$ may be the same or different and are alkyl groups aptly containing up to 6 carbon atoms. Preferably the hydroysable alkoxy or acyloxy group is a $C_1$–$C_3$ hydrocarbon group. More preferably the hydrolysable group is a $C_1$–$C_3$ hydrocarbon alkoxy group and most preferably the hydrolysable group is an ethoxysilyl or methoxysilyl group.

During the curing reaction of the prepolymers the alkoxy or acyloxy silane groups are hydrolysed to form hydroxysilane groups which condense together. The reaction may be exemplified by the following formulae:

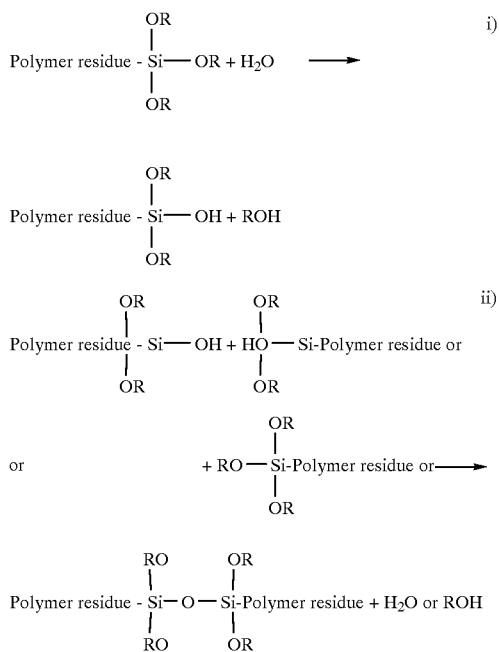

until all or most of the SiOR have reacted to give a crosslinked system.

The resins system for use in the invention can be made by a nucleophilic addition reaction. Suitable examples of nucleophilic addition reactions are Michael-Type reactions and the reaction of nucelophiles with activated carbon-carbon based moieties.

Michael-Type reactions may be defined as the reaction of a nucleophile with an α, β-unsaturated carbonyl moiety. Michael-Type reactions may be exemplified by the reaction of acrylates or acrylamides with reagents terminated with —SH, —NH$_2$, —NH—NH$_2$, >NH moieties.

According to an embodiment of the present invention suitable Michael-Type reactions include the reaction of acrylate or acrylamide reagents with reagents terminated with —SH, —NH$_2$, —NH—NH$_2$, >NH moieties where at least one of the reagents is further terminated with an alkylenesilane group.

The preferred Michael-Type reactions include the reaction of aminoalkylenesilanes with acrylates or acrylamides. Most suitably methacrylates, bisphenol A ethoxylate diacrylates and methylene bisacrylamides are employed for reaction with aminoalkylenesilanes.

In another embodiment of the present invention apt nucleophilic reactions comprise the reaction of nucleophiles with activated carbon-carbon based moieties. These include the reaction of reagents terminated with three membered heterocycles with reagents terminated with —SH—, —NH$_2$, —NH—NH$_2$, >NH moieties where at least one of the reagents is further terminated with an alkylenesilane group.

The preferred reactions include the reaction of aminoalkylenesilanes with reagents terminated with three membered heterocycles such as epoxides or aziridenes.

Preferably the reagents terminated with three membered heterocycles are epoxides.

Suitable alkylenesilane terminated reagents are from the group comprising: 3-aminopropyltrimethoxysilane, 3-aminopropyltriethoxysilane, bis(trimethoxysilylpropyl) amine, bis(triethoxysilylpropyl)amine,γ-glycidoypropyltrimethoxysilane and γ-methacryloxypropyltrimethoxysilane.

The resin system of the present invention can also be prepared by employing a mixture of the reactions as herein before described. The preparation of the prepolymer may be catalysed.

Suitable nucleophilic addition acceptors, such as acrylates, acrylamides and epoxides have a reaction functionality of at least 2 and will preferably be hydrophilic enough to render the resin system water absorbent to facilitate the hydrolysis of the silane groups when it is desired to cause the resin system to set.

The preferred prepolymers resin systems are free of isocyanate moieties and thus any perceived health hazards associated therewith are avoided.

The hydrolysis reaction of the alkoxy or acyloxy silane group may be catalysed. Suitable catalysts when the silane end group is an alkoxy derivative may be a de-alcholising agent. When the silane end cap grouping contains an acyloxy group or other group capable of hydrolysing to give an acidic compound the catalyst may be an acid scavenging or neutralising agent. In a preferred embodiment of the invention the end cap grouping will be a $C_1$–$C_3$ hydrocarbon alkoxy silane or an acyloxy silane, more preferably an ethoxy or methoxy silane and the catalysts include organotin salts, chloroacetic acid, methane sulphonic acid (MSA), phosphoric acids, 1,5-diazabicyclo[4.3.0]non-5-ene (DBN), 1,8-diazabicyclo[5.4.0]undec-7-ene (DBU), p-toluene sulphonic acid and bismorpholino dialkyl ethers such as dimorpholinodiethylether.

The catalyst may be present as a single chemical species or a mixture and, when used, is aptly present in an amount of up to 20% w/w, more aptly up to 10% w/w and most preferably up to 5% w/w of the resin. Aptly it should be at least 0.1% w/w of the resin.

The resin system used in the invention may be precured by the addition of water to cross-link a small percentage of the available silane groups. The advantage gained would be an increase in molecular weight, leading to an increase in viscosity.

Preferred formulations of the resin system according to the present invention can include a variety of additives conventional in the art. These additives may comprise fillers, pigments, fragrances, surfactants, lubricants or mixtures thereof.

Suitable powdered fillers include talc, calcium carbonate, fumed silica sold under the trade name Cab-o-Sil™, alumina and fibrous reinforcing fillers such as wollastonites (calcium metasilicate), to impart desirable viscosity and handling characteristics.

The fillers may be present as single chemical species or as mixtures and, when used, are aptly present in an amount of up to 50% w/w, preferably up to 20% w/w and aptly at least 1.0% w/w of the resin.

The resin system used in the bandages of the invention according to the invention may be carried on any substrate suitable for a casting, splinting or bracing material.

In a further embodiment of the present invention there is also provided an orthopaedic splinting material comprising a flexible substrate and a curable silane functionalised resin, characterised in that the resin comprises a prepolymer of the formula (I):

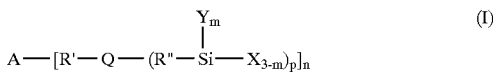

(a) wherein A is a polymeric residue, optionally interrupted by

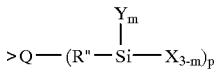

(b) X comprises a water hydrolysable alkoxy or acyloxy group based on $C_1$ to $C_6$ hydrocarbon group
(c) Y is H, alkyl, aryl, halide, X based on $C_1$ to $C_6$ hydrocarbon group
(d) n=1 to 20, m=0 to 2, p=1 to 2
(e) Q comprises residues based on the following formulae (II)

where G=—CH(OH)—, —C(O)—, —CH($NH_2$)—, —CH(SH)— D is —NH—, —N<, —O—, —S— and q=1 or 2
(f) R' and R" may be the same or different, substituted or unsubstituted and are are groups based on the following $C_1$–$C_{12}$ alkylene, arylene, cycloalkylene, heteroalkylene, heteroarylene, heterocycloalkylene all of which may be optionally interrupted by —O—, —S—, —NH—, —C(O)—, further units of Q, with the proviso that urea —NHC(O)NH—, urethane —NHC(O)—, carbamylthio —SC(O)NH— are not represented.

The prepolymers employed in the present invention are end capped with a silane residue containing a hydrolysable group (X). Aptly the hydrolysable group is an alkoxy or acyloxy group.

Favoured end capping groups have the general formula —Si(OR)$_n$, —Si(OCOR)$_n$, —Si—O—Si(OR)$_n$, —Si—O—Si($R_1$)$_{3-n}$(OR)$_n$, —Si(OC($R_3$)=C($R_1$)($R_2$)$_n$, where n has a maximum value of 3 and each of R, $R_1$, $R_2$ and $R_3$ may be the same or different and are alkyl groups aptly containing up to 6 carbon atoms. Preferably the hydroysable alkoxy or acyloxy group is a $C_1$–$C_3$ hydrocarbon group. More preferably the hydrolysable group is a $C_1$–$C_3$ hydrocarbon alkoxy group and most preferably the hydrolysable group is an ethoxysilyl or methoxysilyl group.

The resin system employed in the invention may be coated, laminated, sprayed or impregnated onto a suitable substrate using conventional methods in the art. Aptly the bandages of the invention are prepared by nip-coating the resin system on to the substrate.

A preferred substrate is a flexible fabric carrier which may be a woven, knitted or non woven fabric which can carry enough of the resin system of the invention to ensure that the resultant cast has adequate strength. The substrate should be sufficiently porous to allow water to come into contact with the carried resin when the formed bandage is immersed in water. The substrate may be in the form of tapes, bandages, sheets or other conventional forms, apt for preparing orthopaedic casting bandages, splinting materials or braces.

Suitable materials for forming the substrate include polyester, nylon, polypropylene, polyamides, polyolefins and glass fibre or mixtures thereof. Examples of such substrates are disclosed in Patent Nos. U.S. Pat. No. 4,427,002, U.S. Pat. No. 4,627,424 and EP 326,285.

Aptly the substrate may be a mesh having openings through it to enable the water to penetrate into the rolled bandage to contact all parts of the resin system. The openings will also permit circulation of air to and evaporation of moisture from the skin beneath the cured cast.

Preferably the mesh is of a loose weave or knit so as to allow at least partial impregnation as well as coating by the resin system.

The amount of resin carried by the substrate may vary depending on the instrinsic properties of the resin system and should be sufficient to ensure that the resultant cast has adequate strength.

Suitable amounts range from 30 to 70% w/w of the resin system which is calculated using the equation:

$$\frac{\text{weight of (substrate + resin)} - \text{weight of (substrate)} \times 100}{\text{weight of (substrate + resin)}}$$

Preferably 40 to 65% w/w and most preferably 50 to 60% w/w of the resin system are used.

The bandages of the invention may be used to form a hardened cast by wetting and shaping the wet material around a body member or part thereof and allowing the bandage to cure.

Aptly wetting is achieved by immersing the bandage in water, and removing any excess water, for example, by squeezing the bandage several times before application to the body member.

When removed from the water the bandage can be readily wrapped about a limb wherein the conventional underlying stockinette or padding is employed.

An alternative method for forming a cast or splint comprises applying the bandage of the invention material to the body member followed by spraying the material with water.

The curing reaction of the resin system should be sufficiently slow to allow the bandage of the invention to be positioned and shaped before the bandage becomes unworkable. Suitable working times are aptly 1 to 6 minutes more aptly 2 minutes to 4 minutes. The curing reaction of the resin system should, however, be sufficiently fast to permit the formed cast or splint to become supportive and load-bearing as soon as possible after completion of working. Aptly the bandage will set and become supportive between 5 and 30 minutes, more aptly within 15 minutes and particularly in the case of a cast, will aptly become load-bearing within 60 minutes, more aptly after 10 minutes.

The resin systems employed in the present invention possess the further advantage in that the curing reaction is only slightly exothermic thus causing no harm or discomfort to the patient.

The cast may be readily removed by conventional means such as by cutting with a convention vibrating sawtooth disc.

The orthopaedic casting bandage of the invention should be protected during storage from water and moisture vapour to prevent a premature setting taking place. The bandage can be conventionally packaged in heat sealed pouches such as metal foil polyethylene laminate pouches.

The invention will now be described by way of the following example only and it should be understood that normal precautions for excluding moisture during chemical reactions were employed.

The resin systems as described in the following preparations were coated onto dry glass fibre bandages by passing the substrate through the resin system followed by passing the coated bandage through a nip roller, adjusted to a suitable pressure for obtaining a coating weight of 50–60% w/w coating. The resin was set of by dipping the coated bandage in cold water, and squeezing several times before application to a mandrel representing a limb.

PREPARATION 1

3-Aminopropyltrimethoxysilane (70 g) was mixed with methylene bisacrylamide (30 g) in an oven dried jar. The mixture was stirred and heated at 50° C. for a total of 6 hours. The heating was carried out intermittently over a period of 5 days. After this time a prepolymer was formed.

PREPARATION 2

3-Aminopropyltriethoxysilane (141 g) was mixed with methylenebisacrylamide (70g) and reacted, with stirring, at 50° C. for 4 days, in a sealed vessel. After this time, a prepolymer had formed.

PREPARATION 3

Sartomer 344 (33.6 g) and bis(trimethoxysilylpropyl) amine (40.5 g) were mixed thoroughly in a sealed jar and allowed to stand for 48 hours. A prepolymer was formed.

PREPARATION 4

Sartomer (344) (33.6 g) and bis(trimethoxysilylpropyl) amine [A-1170] (40.5 g) were mixed thoroughly in a sealed jar and allowed to stand for 48 hours. A prepolymer was formed and prior to coating was mixed with filler, Cab-o-Sil™ (5% w/w), to form a resin system.

PREPARATION 5

Saromer 344 (62.4 g), piperazine (4.7 g) and A-1170 (37.4 g) in a ratio of 2:1:2, were mixed on an oven dried glass jar, sealed and rolled for several hours until the piperazine had all disolved. It was then allowed to stand for 48 hours, and a prepolymer was formed.

PREPARATION 6

As Preparation 5, with a molar ratio of Sartomer 344, piperazine and A-1170 of 3:2:2.

PREPARATION 7

Bisphenol A ethoxylate diacrylate (98.6 g) was mixed with 3-aminopropyltrimethoxysilane (51.4 g) in a sealed jar and allowed to stand for 48 hours. A prepolymer was formed.

PREPARATION 8

Bisphenol A ethoxylate diacrylate (91.3 g) was mixed with 3-aminopropyltriethoxysilane (58.7 g) in a sealed jar and allowed to stand for 48 hours. A prepolymer was formed.

PREPARATION 9

Bisphenol A ethoxylate diacrylate [4EO/phenol] (75.3 g) was mixed with A-1170 (74.7) in a sealed jar and allowed to stand for 48 hours. A prepolymer was formed.

PREPARATION 10

Crodamer UVM45 (71.6 g) and 3-aminopropyltrimethoxysilane (78.4 g) were mixed in a sealed jar and allowed to stand for 48 hours. A prepolymer was formed.

PREPARATION 11

Crodamer UVM45 (63.9 g) and 3-aminopropyltriethoxysilane (86.1 g) were mixed in a sealed jar and allowed to stand for 48 hours. A prepolymer was formed.

PREPARATION 12

Crodamer UVM45 (48.7 g) and A-1170 (101.3 g) were mixed in a sealed jar and allowed to stand for 48 hours. A prepolymer was formed.

PREPARATION 13

1,3-Diaminopropane (0.3 g), Crodamer UVM45 (6.8 g), 3-aminopropyltrimethoxysilane (7.9 g) and Jeffamine EDR148 (15%/w) were mixed at room temperature, sealed and allowed to stand for 48 hours. A prepolymer was formed. Prior to coating, the resin (14.9 g) was mixed with methanesulphonic acid (0.1 g) and filler Scotchlite K37 (1 g), to form a resin system.

PREPARATION 14

Bisphenol epoxide EP519 (19.5 g) and 3-aminopropyltrimethoxysilane (20.5 g) were reacted in a 100% solids reaction by mixing the reagents under nitrogen in a dry glass vessel which was subsequently sealed and heated in an oven at 55° C. for 16 to 20 hours, to form a prepolymer.

PREPARATION 15

Bisphenol epoxide NPES601 (17.5 g) and A-1170 (32.5 g) were reacted as in Preparation 14 to form a prepolymer.

PREPARATION 16

Bisphenol epoxide EP519 (13.3 g) and A-1170 (26.7 g) were reacted as in Preparation 14 to form a prepolymer.

PREPARATION 17

Bisphenoldiacrylate (13.1 g) and 3-aminopropyltrimethoxysilane (6.8 g) were reaced in a 100% solids reaction by mixing the reagents under nitrogen in a dry glass vessel which was subsequently sealed and left to stand at room temperature for 16 to 20 hours, to form a prepolymer.

PREPARATION 18

Sartomer 454 (30.7 g) and 3-aminopropyltrimethoxy silane (19.3 g) were reacted as in Preparation 17 to form a prepolymer.

PREPARATION 19

Bisphenol A diacrylate [4EO/phenol] (268.3 g) and 3-aminopropyltrimethoxysilane (231.3 g) were reacted by mixing the reagents in a sealed jar and allowed to stand for 48 hours. A prepolymer was formed which was subsequently precured by the addition of water (2.3 g).

Materials used in the above Preparations:
3-Aminopropyltrimethoxysilane is 3-APTMS, obtainable from Hüls UK.
3-Aminopropyltriethoxysilane, obtainable from Hüls UK.
Bis(trimethoxysilylpropyl) amine is A1170, obtainable from Osi specialties.
Methylene bisacrylamide, obtainable from Aldrich Chemical Co. Sartomer 344 is poly(ethyleneglycol) 400 diacrylate obtainable from Cray Valley Total.

Crodamer UV45 is ethoxylated pentaerythritol tetracrylate obtainable from Croda Resins.

Jeffamine EDR148 is a polyethylene glycol diamine, obtainable from Huntsman corporation.

Bisphenol A ethoxylate diacrylate [4EO/phenol], obtainable from Aldrich Chemical Co.

Piperazine, obtainable from Aldrich Chemical Co.

EP519 is a bisphenol epoxide, obtainable from Whyte Chemicals.

Sartomer 454 is an ethoxylated trimethylol propane triacrylate, obtainable from Cray Valley Total.

KL26 is dimorpholinodiethylether obtainable from Zeeland Chemicals.

Cab-o-Sil™ is fumed silica obtainable from Cabot Corp (USA)

Scotchlite K37 are hollow glass spheres obtainable from 3M(UK).

We claim:

1. An orthopaedic casting bandage comprising a flexible substrate carrying curable silane functionalised resin system, characterised in that the resin system comprises a prepolymer of the formula (I):

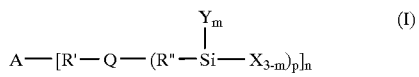
$$A\text{—}[R'\text{—}Q\text{—}(R''\text{—}\underset{|}{\overset{Y_m}{Si}}\text{—}X_{3-m})_p]_n \qquad (I)$$

(a) wherein A is a polymeric residue, optionally interrupted by

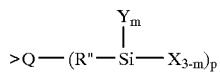
$$>Q\text{—}(R''\text{—}\underset{|}{\overset{Y_m}{Si}}\text{—}X_{3-m})_p$$

(b) X comprises a water hydrolysable alkoxy or acyloxy group based on $C_1$ to $C_6$ hydrocarbon group (c) Y is H, alkyl, aryl, halide, X based on $C_1$ to $C_6$ hydrocarbon group (d) n=1 to 20, m=0 to 2, p=1 to 2

(e) Q comprises residues based on the following formulae (II)

$$\text{—G—}(CH_2)_q\text{—D— or —D—}(CH_2)_q\text{—G—} \qquad (II)$$

where G=—CH(OH)—, —C(O)—, —CH(NH$_2$)—, —CH(SH)— D is —NH—, —N<, —O—, —S— and q=1 or 2

(f) R' and R'' may be the same or different, substituted or unsubstituted and are groups based on the following $C_1$–$C_{12}$ alkylene, arylene, cycloalkylene, heteroalkylene, heteroarylene, heterocycloalkylene all of which may be optionally interrupted by —O—, —S—, —NH—, —C(O)—, further units of Q, with the proviso that urea —NHC(O)NH—, urethane —NHC(O)—, carbamylthio —SC(O)NH— are not represented.

2. A bandage according to claim 1 wherein the water hydrolysable group is from the group comprising (OR), (OCOR), (OC($R_3$)=C($R_1$)($R_2$)) or mixtures thereof where R, $R_1$, $R_2$, $R_3$ may be the same or different and are based on $C_1$ to $C_6$ hydrocarbon group.

3. A bandage according to claim 1 wherein the water hydrolysable alkoxy or acyloxy group is a $C_1$ to $C_3$ hydrocarbon group.

4. A bandage according to claim 1 wherein the water hydrolysable alkoxy group is an ethoxy group.

5. A bandage according to claim 1 including a catalyst to catalyze the polymerisation reaction of the silane functionalised prepolymer with water.

6. A bandage according to claim 5 wherein said catalyst is from the group comprising:

methane sulphonic acid, 1,5-diazabicyclo[4.3.0] non-5-ene 1,8-diazabicyclo[5.4.0]undec-7-ene ethyl titanate p-toluene sulphonic acid dibutyltindilaurate, or mixtures thereof.

7. A bandage according to claim 5 wherein said catalyst is present in an amount up to 20% w/w of the resin.

8. A bandage according to claim 1 including a filler.

9. A bandage according to claim 6 wherein said filler is fumed silica.

10. A bandage according to claim 1 including additions comprising pigments, fragrances, surfactants, lubricants or mixtures thereof.

11. A bandage according to claim 1 within the resin system is coated onto the flexible substrate.

12. A bandage according to claim 11 wherein the coating comprises a weight of 30 to 70% w/w.

13. A bandage according to claim 1 wherein the flexible substrate is a woven, knitted or non woven fabric.

14. A bandage according to claim 13 wherein the flexible substrate comprises polyester, nylon, polypropylene polyamides, polyolefins, glassfibre or mixtures thereof.

15. A method for applying an orthopaedic casting bandage according to claim 1 comprising wetting the bandage, shaping the bandage around a bodymember and allowing the resin system to cure.

16. An orthopaedic splinting material comprising a flexible substrate carrying a water curable silane functionalised resin as defined in claim 1.

17. An article comprising a water curable silane functionalised resin as defined in claim 1.

18. The use of a water curable silane functionalised resin as defined in claim 1 in an orthopaedic casting bandage or splint.

* * * * *